(12) United States Patent
Tobón Gómez et al.

(10) Patent No.: US 12,376,813 B2
(45) Date of Patent: Aug. 5, 2025

(54) METHOD AND DEVICE FOR MONITORING A FLOW OF A FLUID IN A VESSEL

(71) Applicant: Medis Associated B.V., Leiden (NL)

(72) Inventors: Catalina Tobón Gómez, Haarlem (NL); Hua Ma, Rotterdam (NL); Johannes Petrus Janssen, Leiden (NL); Gianni Pedrizzetti, Florence (IT); Johan Hendrikus Christiaan Reiber, Rotterdam (NL); Yves Robèrt Vijgeboom, Geleen (NL)

(73) Assignee: QFR SOLUTIONS B.V., Leiden (NL)

( * ) Notice: Subject to any disclaimer, the term of this patent is extended or adjusted under 35 U.S.C. 154(b) by 406 days.

(21) Appl. No.: 17/980,108

(22) Filed: Nov. 3, 2022

(65) Prior Publication Data

US 2023/0135309 A1    May 4, 2023

(30) Foreign Application Priority Data

Nov. 4, 2021    (NL) ...................................... 2029633

(51) Int. Cl.
*A61B 6/50*     (2024.01)
*A61B 6/00*     (2006.01)

(52) U.S. Cl.
CPC .............. *A61B 6/504* (2013.01); *A61B 6/481* (2013.01); *G06T 2207/30101* (2013.01)

(58) Field of Classification Search
CPC .................................................. G06T 7/0012
See application file for complete search history.

(56) References Cited

U.S. PATENT DOCUMENTS

| 10,687,774 | B2 | 6/2020 | Lautenschläger | |
| 2004/0265393 | A1* | 12/2004 | Unger | A61K 41/0028 604/20 |
| 2018/0099125 | A1* | 4/2018 | Richer | A61M 25/09041 |

(Continued)

FOREIGN PATENT DOCUMENTS

| CN | 113887463 A | * | 1/2022 | |
| JP | 2022095470 A | * | 6/2022 | ............. A61B 6/461 |

(Continued)

OTHER PUBLICATIONS

Gibson et al., TIMI Frame Count, A Quantitative Method of Assessing Coronary Artery Flow; vol. 93, Issue 5, Mar. 1, 1996; pp. 879-888.

(Continued)

*Primary Examiner* — Di Xiao
(74) *Attorney, Agent, or Firm* — Banner & Witcoff, Ltd.

(57) ABSTRACT

A method is provided for monitoring a flow of a fluid in a vessel of a body of a living being is provided. The method comprises obtaining a first image data set representing the vessel filled with a first fluid, the first image data set comprising at least one first image frame and the first fluid contrasting with matter surrounding the vessel and obtaining a second image data set representing the vessel substantially void of the first fluid, the second image data set comprising at least one second image frame. Based on the first image data set and the second image set, an estimated location of the vessel in the second image set is estimated; and monitoring presence in the second data set of contrasting image data at the estimated location of the vessel is monitored.

19 Claims, 3 Drawing Sheets

(56) References Cited

U.S. PATENT DOCUMENTS

| | | |
|---|---|---|
| 2019/0029624 A1 | 1/2019 | Kunio |
| 2020/0222018 A1 | 7/2020 | van Walsum et al. |
| 2022/0343494 A1* | 10/2022 | Dhatt .................... A61B 8/467 |

FOREIGN PATENT DOCUMENTS

| | | |
|---|---|---|
| WO | 2019210553 A1 | 11/2019 |
| WO | 2022086326 A1 | 4/2022 |

OTHER PUBLICATIONS

Dutch Search Report and Written Opinion—App No. 2029633—mailing date Jul. 20, 2022.
Hentschke, Clemens M. et al., "Estimating blood flow velocity in angiographic image data," Proc. of SPIE vol. 7964, pp. 1-9 (2011).
Bogunović, Hrvoje et al., "Blood Flow and Velocity Estimation Based on Vessel Transit Time by Combining 2D and 3D X-Ray Angiography," MICCAI 2006, LNCS 4191, pp. 117-124 (2006).

* cited by examiner

METHOD AND DEVICE FOR MONITORING A FLOW OF A FLUID IN A VESSEL

CROSS-REFERENCE TO RELATED APPLICATIONS

This application claims priority under 35 U.S.C. § 119 to Application NL 2029633, filed Nov. 4, 2021, which is hereby incorporated by reference in its entirety.

TECHNICAL FIELD

The various aspects and variations thereof relate to tracking of flow of a fluid through a vessel of a living being.

BACKGROUND

For determining various parameters of a cardiovascular system, like fractional flow reserve, flow velocity of blood in a coronary vessel may be required. The flow velocity may be determined as described in "*TIMI Frame Count*" by C. Michael Gibson e.a. as published in Circulation 1996; 93: 879-888.

SUMMARY

It is preferred to provide an efficient basis for tracking of a bolus of contrast dye in a vessel in a body and in a coronary vessel in particular. To this end, in a first aspect, a method of monitoring a flow of a fluid in a vessel of a body of a living being is provided. The method comprises obtaining a first image data set representing the vessel filled with a first fluid, the first image data set comprising at least one first image frame and the first fluid contrasting with matter surrounding the vessel and obtaining a second image data set representing the vessel substantially void of the first fluid, the second image data set comprising at least one second image frame. Based on the first image data set and the second image set, an estimated location of the vessel in the second image set is estimated; and monitoring presence in the second data set of contrasting image data at the estimated location of the vessel is monitored.

A vessel filled with contrast dye is well visible using imaging technology like computer tomography and x-ray imaging. With image data of the vessel acquired while the vessel is filled provides data on geometry and location of the vessel. Based thereon, an estimate of at least one of geometry and location of the vessel in the second image data set may be provided. Subsequently, while tracking progress of contrast dye in the second image data set by detecting image pixels with contrasting image data for one or more image may only, firstly or primarily be done at and, optionally, around, the estimated location and geometry of one or more images of the second image data set. This means that not all pixel of images in the second image data set may have to be analysed for tracking progress of the contrast dye through the vessel.

In a variation, the first data set comprises a multitude of first image frames, the first image frames having been acquired consecutively in time; and the second data set comprises a multitude of second image frames, the second image frames having been acquired consecutively in time. In this variation, the method further comprises tracking, in the first data set, the vessel over time and estimating, based on the tracking, over time, a location of the vessel in the second frames of the second data set. The estimation of at least one of the geometry and location of the vessel may be done statically and this variation relates to tracking of at least one of the geometry and location over time. In particular a coronary vessel moves and changes in shape over the course of a heartbeat, for which reason it may be preferred to track the vessel over time and estimate geometry and/or location over time.

In another variation, the first data set is acquired over a first time interval relative to a heartbeat sequence, the second data set is acquired over a second time interval relative to the heartbeat sequence and the first time interval and the second time interval cover at least one equivalent part of the heartbeat sequence. With both the first image data set and the second image data set comprising equivalent parts or equivalent phases of a hearts, both the image data sets may be aligned over time, such that at least one of location and geometry of the vessel may for example be estimated in an image of the second set, based on an image in the first in set at an equivalent moment in a heartbeat sequence, at which moment it is probable that at least one of geometry and location of the vessel is substantially the same in the second set as it is depicted in the first set.

In a further variation, the first timer interval and the second timer interval cover at least one heartbeat sequence. An advantage thereof is that the image sets cover a full sequence, providing generally all possible shapes and locations of the vessel, as possibly modified by the heartbeat.

Again another variation comprises aligning the first image data set and the second image data set based on heartbeat sequence data associated with the first image data set and the second image data set, associating frames in the first image data set and the second image data set with a particular phase in the heartbeat sequence and estimating, over time, estimated locations of the vessel in the second frames of the second image data set based on locations of the vessel in the first frames of the first image data set having substantially the same phase in the heartbeat sequence associated therewith as with the second frames. This variation is a practical implementation of the previous ones, reducing complexity and increasing accuracy of the estimation.

In a further variation, the first image data set and the second image data set have electrocardiogram data as heartbeat sequence data associated therewith. An advantage is that an ECG provides easy to process and well-known data on phases in a heartbeat sequence.

In yet a further variation, heartbeat sequence data is derived from image frame data in at least one of the first image data set and the second image data set. For example, from a shape of a coronary vessel, a phase in a heartbeat sequence may be estimated, as such shape varies in a periodic way over the sequence of a heartbeat. The moment in the sequence may be obtained by (directly) comparing the obtained image to one or more reference images. Additionally or alternatively, the applicable image may be provided to a trained neural network or other artificial intelligence capable of at least one of image recognition and image classification.

In yet another variation, the tracking of the vessel over time comprises identifying a multitude of points of interest distributed on a representation of the vessel in the first image frames and tracking locations of the points of interest in the applicable image over time.

Again a further variation comprises reconstructing the vessel geometry over time. Whereas this variation may consume a considerable amount of memory and processing power, it may provide more accuracy.

In yet again a further variation, the reconstructing comprises determining a centreline of the vessel in the image data. By representing the vessel by means of a centreline only, an efficient representation may be provided. Alternatively, the centreline may be used as a basis for a more advanced or more sophisticated representation of the vessel.

Another variation further comprises reconstructing a vessel geometry based on the first image data set and estimating a location of the vessel in the second image set based on the first image data set and the reconstructed vessel geometry. With a vessel geometry available, estimation of the vessel location and locations of multiple points of the vessel geometry in particular, only a few points of the vessel location in the second image data set need to be identified, for example estimated, upon which the vessel geometry may be fit to those locations. As a result, the full location of the full geometry is efficiently estimated.

In yet another variation, the first image set comprises a first image subset comprising at least a first image acquired under a first angle relative to the living being; and a second image subset comprising at least a second image acquired under a second angle relative to the living being; in this variation, the reconstructed vessel geometry is a three-dimensional geometry. With a three-dimensional representation, more accuracy may be provided.

In yet again another variation, the second image set comprises a first image subset comprises at least a first image acquired under the first angle relative to the living being; and a second image subset comprises at least a second image acquired under the second angle relative to the living being; in this variation, the estimated location of the vessel in the second image set is a three-dimensional location. With a three-dimensional representation of the location, more accuracy may be provided.

A further variation further comprises determining a first length of the vessel as depicted by the first image subset, determining a second length of the vessel as depicted by the second image subset, determining a natural length of the reconstructed vessel, selecting the first image subset if the first length is closer to the natural length or selecting the second image subset if the second length is closer to the natural length, estimating the location of the vessel in the second image data set based on the subset of the first dataset of which the length is closest to the natural length. A longer length enables analysis with a higher resolution.

In another variation, the location in the second image data set is determined based on the image subset corresponding to the image subset of the first image data set depicting a length closest to the natural length. This may also provide an improved resolution.

In yet a further implementation, the vessel is filling with the first fluid while the second dataset is acquired. This variation allows for determining transit time of a front of a bolus with contrast dye. With this data, transit velocity of a body fluid through the vessel, for example blood, may be determined. In a coronary vessel, this transit velocity or flow rate may be used for determining fractional flow reserve of a vessel, or a related or derivative value of the fractional flow reserve.

In again another variation, the second image data set is acquired prior in time relative to the acquiring the first image data set. This variation requires contrast dye as an example of the first fluid or first liquid to be inserted in the vessel only once for the analysis in accordance with the first aspect.

The first aspect, with all its variations indicated above and below, may be employed in a method of determining vessel fluid flow velocity of a fluid in a vessel segment of a body of a human or another mammal. The method comprises obtaining a natural length model of the vessel representing a length of the length of the vessel in accordance with the method according to any variation of the first aspect, obtaining a two-dimensional model of the vessel segment based on the first image dataset, dividing the two-dimensional model in vessel sections, receiving the second dataset comprising a multitude of second image frames, the second image frames having been acquired consecutively in time, based on the images of the second dataset, assigning, for each image of the set, at least one intensity value to each vessel section, identifying, in a first image related to a first moment in time, a first vessel section, based on an intensity criterion, identifying, in a second image related to a second moment in time, a second vessel section, based on the intensity criterion, the second moment in time being later than the first moment in time and the second vessel section being distal to the first vessel section, obtaining a propagation length by relating the first vessel section and the second vessel section to the natural length and determining a vessel fluid flow velocity based on the propagation length, and a difference between the first moment in time and the second moment in time.

A second aspect provides a computer programme product comprising computer executable code that cause a computer, when the instructions are loaded in a memory connected to a processing unit comprised by the computer, cause the computer to execute the method according to the first aspect or any of the variations discussed above and below.

A third aspect provides a non-transitional medium having stored thereon the computer programme product according to the second aspect.

A fourth aspect provides a device for monitoring a flow of a fluid in a vessel of a body of a living being. The device comprises an input module arranged to obtain a first image data set representing the vessel filled with a first fluid, the first image data set comprising at least one first image frame and the first fluid contrasting with matter surrounding the vessel; and obtain a second image data set representing the vessel substantially void of the first fluid, the second image data set comprising at least one second image frame; and a processing unit arranged to: estimate, based on the first image data set and the second image set, an estimated location of the vessel in the second image set; and monitor presence in the second image data set of contrasting image data at the estimated location of the vessel. As such, the fourth aspect also relates to a device for executing the method according to the first aspect or any variation thereof.

BRIEF DESCRIPTION OF THE DRAWINGS

The various aspects and implementations thereof will now be discussed in further detail in conjunction with drawings. In the drawings.

DETAILED DESCRIPTION

Figure 1:
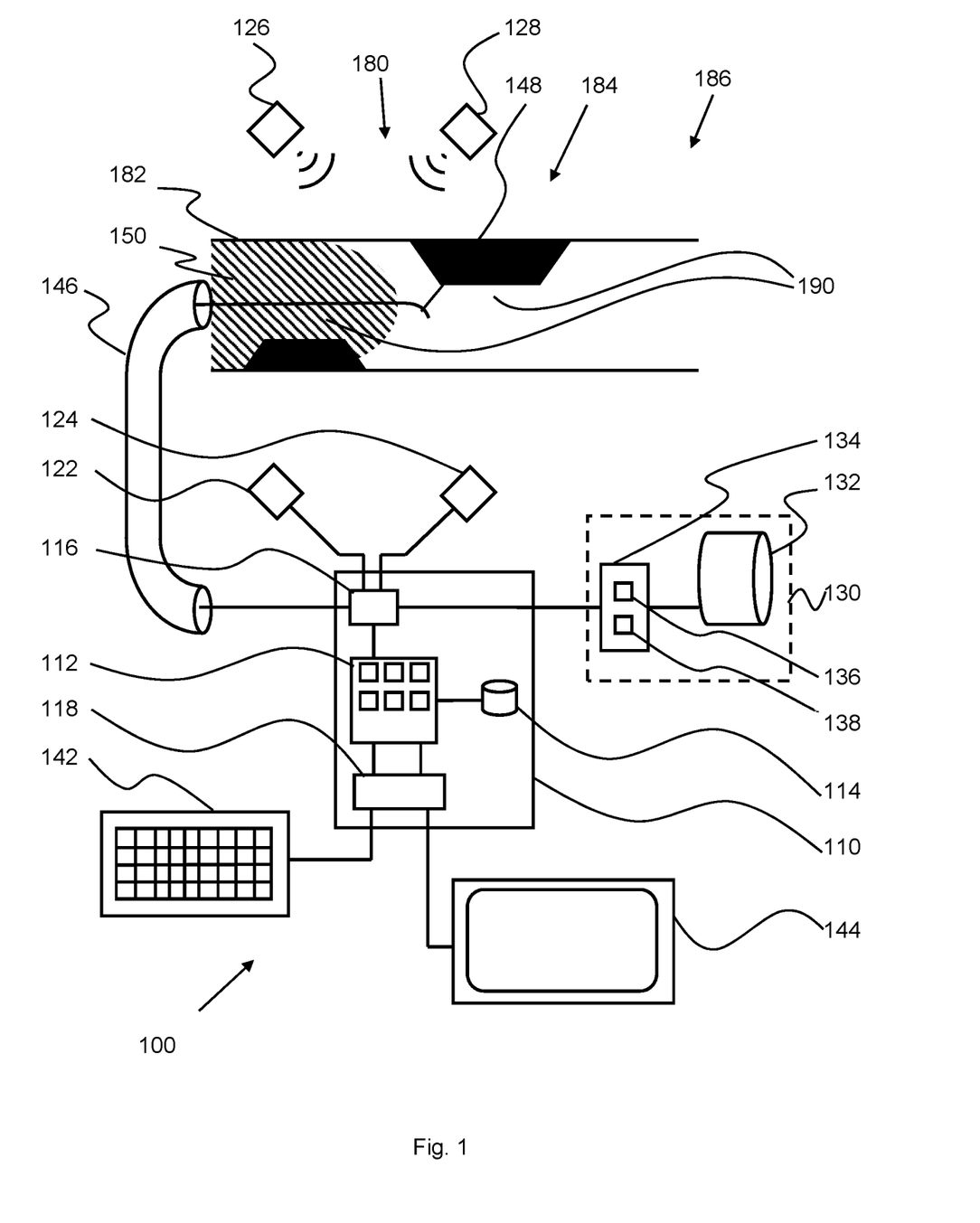
FIG. 1: shows a system for image acquisition and processing.

FIG. 1 shows an electronic medical data acquisition and processing system 100 as an example of the second aspect. The system 100 or parts thereof may be found in a cardiac catheterisation laboratory of a clinic or a hospital. The system 100 comprises an X-ray image acquisition module comprising a first X-ray source 126 and a second X-ray source 128, a first X-ray detector 122 arranged to receive X-ray data from the first X-ray source 126 and a second X-ray sensor 124 arranged to receive X-ray data from the second X-ray source 128. The first X-ray source 126, the second X-ray sensor 124, the first X-ray detector 122 and the second X-ray sensor 124 are arranged to obtain images of a cardiovascular structure 180 under an angle relative to one another. The angle is preferably between 25° and 45°, more preferably between 30° and 40°.

The first X-ray detector 122 and the second X-ray detector 124 are connected to data acquisition module 116 of an electronic computing device 110. The electronic computing device further comprises a processing unit 112, a storage module 114 and a peripherals I/O controller 118. The processing unit 112, which may be implemented as a microprocessor, microcontroller or other electronic data processing device, is arranged to control the various part of the electronic computing device 110 and the system 100 and arranged to execute the method according to the first aspect and implementations thereof.

The storage module 114 is arranged for storing data thereon, for example acquired by the computing device 110 from the various other parts of the system 100, either directly or after processing by the processing unit 112. The storage unit 114, as at least partially implemented as a non-transitional storage medium, is further arranged for storing computer executable code which allow the processing unit 112 to execute the method according to the first aspect and implementations thereof.

The system 100 further comprises, in this implementation as an option, a heartbeat data acquisition module 130 comprising an ECG acquisition contact pad 132, a control unit 134 comprising a pulse sensor 136 and a clock unit 138. The heartbeat data acquisition module 130 is arranged to obtain data related to heartbeat and heartbeat phase data in particular as a function of time. The pulse sensor 136 may be a photoplethysmography unit or another sensor arranged to determine pulse of a person. The control unit 134 is arranged to relate the data acquired by means of the ECG acquisition contact pad 132 and the pulse sensor 136 to time, for example by adding a timestamp.

The system 100 comprises a pressure tip 148 as another blood pressure measurement module, which corresponds to the intracoronary distal pressure. The pressure tip 148, which is connected to a coronary wire, transmits the pressure to the data acquisition module 116, from a coronary artery 182 of the cardiovascular structure 180 as an example of a coronary vessel or blood vessel in general via a catheter 146 inserted in a body of a mammal, like a human being. Additionally, the tip of the coronary catheter 146, placed into the ostium of the coronary artery under scrutiny 182, senses the proximal pressure into the vessel, which corresponds to the aortic pressure. Furthermore, the catheter 146 may be used to insert contrast dye 150 in the coronary artery 182 or another vessel of a body.

The peripherals I/O controller 118 is arranged to connect the computing device 110 and the various components thereof to input device like a keyboard 142 or a touch screen for receiving data like user input. The peripherals I/O controller 118 is arranged to connect the computing device 110 and the various components thereof to output devices like an electronic display 144 and other output devices arranged to provide a user with data on processed or unprocessed data received by the computing device 110.

As shown in FIG. 1, the catheter 146 and the pressure wire 148 are inserted in the coronary artery 182. In the coronary artery 182, narrowings 190 are present. The stenotic areas result in narrowing in the various vessels of the coronary vascular structure 180, which, in turn results in pressure drops at the various stenotic areas. Subsequently, the pressure drops result in reduced perfusion of myocardial tissues, which leads to reduced physical condition of the person under scrutiny. The cardiovascular structure 180 shown by FIG. 1 may be a hypothetical structure and is not necessarily a representation of an actual anatomical structure.

Figure 2:
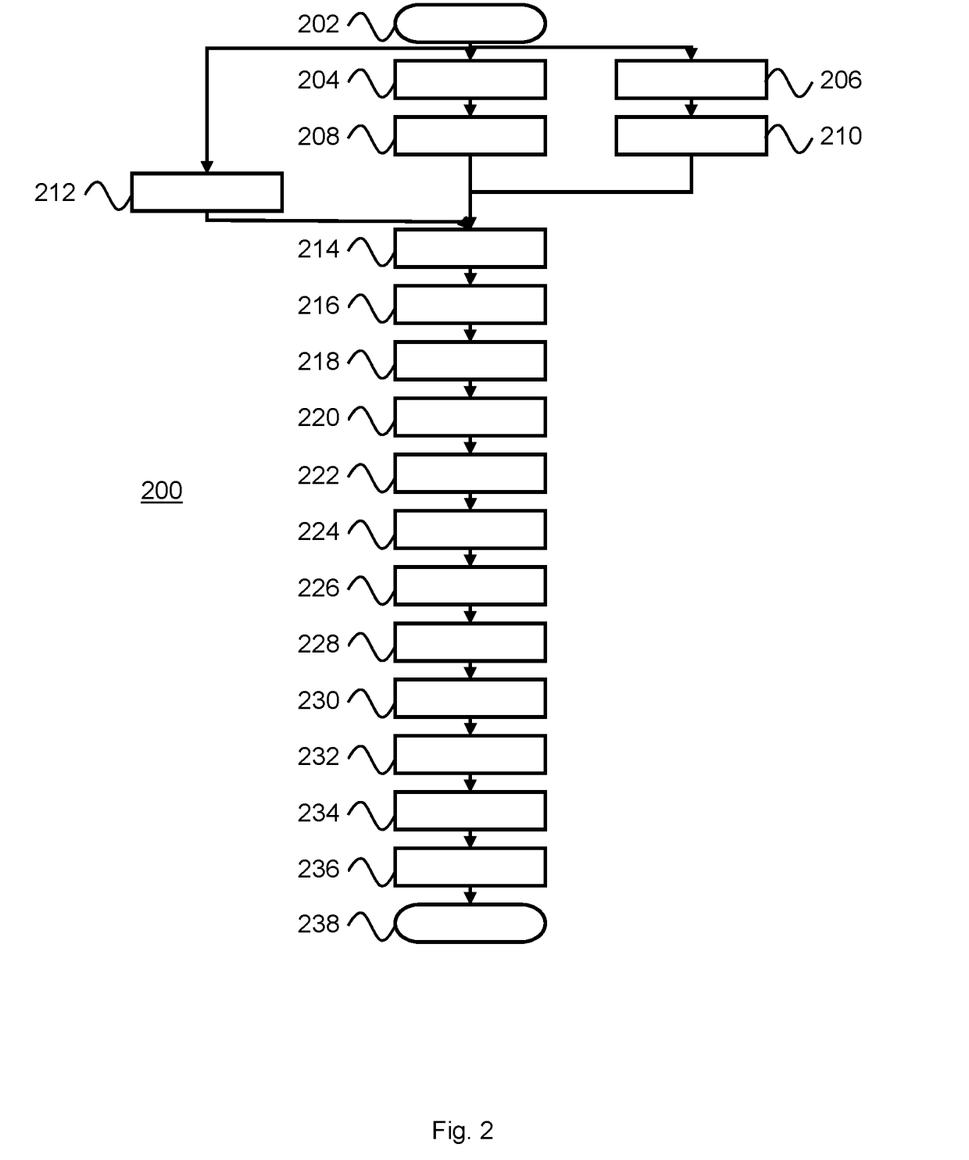
FIG. 2: shows a flowchart.

The further functionality of the system 100 and parts thereof discussed above will be further elucidated in conjunction with a flowchart 200 depicted by FIG. 2. The procedure depicted by the flowchart 200 is executed by the system 100 and the electronic computing device 110 in particular, controlled by the processing unit 112. To provide this functionality, the processing unit 112 may be programmed by means of a computer programme product comprising computer executable code. The computer programme product may be stored on the storage unit 114 as an electronic memory, which may be a non-transitory memory. The various parts of the flowchart 200 are briefly summarised below.

202 start of the procedure
    204 acquire first subset of second image data set
    206 acquire second subset of second image data set
    208 acquire first subset of first image data set
    210 acquire second subset of first image data set
    212 obtain heartbeat phase data
    214 link image data to heartbeat phase data
    216 identify vessel in first subset of first image data set
    218 identify vessel in second subset of first image data set
    220 obtain sensor difference angle between first and second subsets
    222 reconstruct three-dimensional vessel geometry
    224 determine three-dimensional vessel length
    226 determine two-dimensional vessel length first subset
    228 determine two-dimensional vessel length second subset
    230 link vessel geometry to time
    232 link vessel geometry to a location in an image frame in the first data set
    234 associate frames of the second data set to frame of the first data set (based on HB)
    236 link reconstructed vessel geometry and location to image data of the second image data set
    238 monitor image data in the second data set
    238 end procedure The procedure starts in a terminator 202 and continues to step 204 in which a first subset of a second image data set is acquired. In step 204, a second subset of image of the second image data set is acquired. The second image data set is acquired while the contrast dye 150 is provided to the coronary artery 182. As such, the second image data set is acquired while the contrast dye 150 is gradually filling up the coronary artery 182. The first subset of the second image data set is acquired by means of the first X-ray source 126 and the first X-ray sensor 122 and the second subset of the second image data set is acquired by means of the second X-ray source 128 and the second X-ray sensor 124. The first subset and the second subset of the second image data set preferably comprise a multitude of X-ray image frames, acquired at regular intervals in time, as the contrast dye 150 progresses in the coronary artery 182.

In one embodiment, the first X-ray sensor 122 and the second X-ray sensor 124 acquire data at the same moment, for example by acquiring images at substantially the same moment in time. As such, the first subset and the second subset of the second dataset may be streams of image frames.

In step 208, a first subset of a first image dataset is acquired and in step 210, a second subset of the first image dataset is acquired.

The first image data set is acquired while the contrast dye 150 is present through the full length of the coronary artery 182. The second image data set may be acquired prior to the first image data set, allowing second data to be acquired while the coronary artery 182 gradually fills with the contrast dye and to subsequently allow first data, for the first image data set, to be acquired while the coronary artery 182 is substantially full with the contrast dye 150. Working the other way around is possible as well, but would require the coronary artery 182 to be flushed after acquiring the first image data set to get the contrast dye 150 out of the coronary artery 182. The flushing would be required to allow acquisition of the second image data set while the contrast dye 150 is gradually filling the coronary artery 182.

The first subset of the first image data set is acquired by means of the first X-ray source 126 and the first X-ray sensor 122 and the second subset of the first image data set is acquired by means of the second X-ray source 128 and the second X-ray sensor 124. The first subset and the second subset of the first image data set preferably comprise a multitude of X-ray image frames, acquired at regular intervals in time, as the contrast dye 150 progresses in the coronary artery 182.

In one embodiment, the first X-ray sensor 122 and the second X-ray sensor 124 acquire data at the same moment, for example by acquiring images at substantially the same moment in time. As such, the first subset and the second subset of the first dataset may be streams of image frames.

In certain embodiment, no two X-ray sources and no two X-ray sensors are present. In such case, the first subsets and the second subsets are acquired at different intervals in time.

In step 212, heartbeat data of the person under scrutiny is acquired, in this example in parallel to acquisition of the image data. The heartbeat data is acquired by means of the heartbeat data acquisition module 130. The heartbeat data thus acquired is lined up to the image data in step 214. The linking of data may be established in various ways. One option is to assign a momentary ECG value to an image frame acquired at the same moment. Another options is to provide ECG data in a metafile, provided with time data and to provide the image frames of the image data sets with time data such that it matches time data of the ECG data. Additionally or alternatively to ECG data, also photoplethysmography data may be used.

Figure 3:
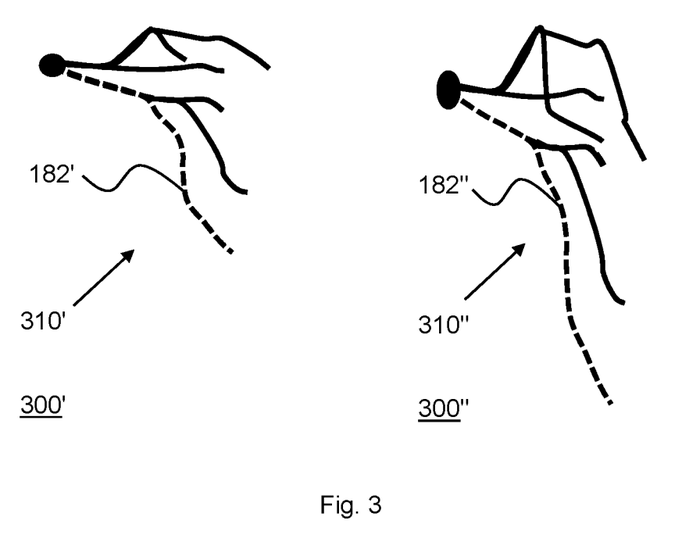
FIG. 3: shows two images of a cardiovascular structure.

In step 216, the coronary artery 182 is identified in the first subset of the first image data set. FIG. 3 shows a first image frame 300' and a second image frame 300". The first image frame 300' is part of the first subset of the first image data set and the second image frame 300" is part of the second subset of the second image data set. The coronary artery 182 is in the first image frame 300' visible as artery image 182' and in the second image frame 300" visible as artery image 182". As such, the coronary artery 182 is identified in the first subset of the first image data set and in the second subset of the first image data set, in step 218.

The coronary artery 182 may be defined in one frame of the first subset, but also from frame to frame, thus tracking the coronary artery 182 from frame to frame to obtain the geometry and location of the coronary artery 182 over time. With such tracking, the full geometry of the coronary artery 182 may be followed from image to image. In another implementation, specific points of the coronary artery 182 or locations on a centreline may be followed from frame to frame. The data acquired by following movements of the points of interest from frame to frame may subsequently be used to reconstruct the coronary artery geometry in one or more frames.

In step 220, the data acquisition angle between the first X-ray detector 122 and the second X-ray sensor 124 is obtained. Using the image data of the coronary artery 182 and the data acquisition angle, the processing unit 112 reconstructs a three-dimensional vessel geometry of the coronary artery 182. In one example, the centreline of the coronary artery 182 is reconstructed in an electronic data file. Additionally or alternatively, a full three-dimensional structure of the coronary artery 182 is reconstructed.

In step 224, the length of the thus reconstructed coronary artery 182 is determined. In one example, the length is determined from the aorta to the final point of the vessel. In step 226, the length of the vessel as depicted by first subset of the first image dataset is determined, for example as depicted by the first image frame 300'. And in step 228, the length of the vessel as depicted by second subset of the first image dataset is determined, for example as depicted by the second image frame 300". The length of the three-dimensional reconstruction is generally the longest, as the natural vessel length.

In step 230, the vessel geometry is linked to timing data. With series of two images acquired at the same moment, from different angles, over a period, a series of three-dimensional reconstructions may be provided. And with timing data as discussed above, each reconstruction may be linked to a moment in time and/or a specific part of a heartbeat cycle. Additionally or alternatively, geometry characteristics like centreline of the vessel identified in the first subset and the second subset of the first set of image data may be linked to timing data.

In step 232, the vessel geometry thus reconstructed—once or multiple times over time—is linked to locations in the image frames of the first subset and the second subset of the first set of image data. In one example, the location of the centreline is associated with the image frames; additionally or alternatively, the full three-dimensional geometry is linked to the image frames.

In step 234, frames of the second set of image data are linked to frames of the first set of image data. The linking is preferably done based on timing data. In particular, frames of the second set of image data are linked to frames of the first set of image data using data related to a phase of a heartbeat. Determining a phase of the heartbeat may be based on the momentary ECG value and, optionally, on analysing the ECG value over time. As such, the P-wave, Q-wave, R-wave and other characteristic points of the ECG data in timing data specifically acquired with the first set of image data and the characteristic ECG data point acquired with the second set of image data may be used to associate particular frames with particular moment or phases in a heartbeat cycle.

Based on the ECG data characteristics, an image frame of the first set of image data may be linked to an image from the second set of image data. More in particular, an image frame of the first subset of the first set of image data may be linked to an image from of the first subset of the second set of image data and an image frame of the second subset of the first set of image data may be linked to an image from of the second subset of the second set of image data. For this matching of frames, it is useful that both the first set of image data and the second set of image data are acquired during the same phases of a heartbeat or overlapping parts of the sequence. It may be even more useful if the acquisition periods for both sets cover at least one heartbeat sequence or more.

Whereas ECG data may be conveniently acquired using relatively common equipment, the heartbeat phase data may be acquired in other ways. In one example, pulse data may be obtained using an optical pulse meter. In another example, the heartbeat phase data may be obtained by analysing image data of the second set of image data. The shape of the location of the coronary artery 182, filled with contrast dye, varies of time during the heartbeat sequence. Hence, from at least one of the shape and location of the coronary artery 182 in frames of the second set of image data, a phase in the heartbeat sequence may be determined. This determination may be executed by means of a model, by comparing image data acquired to stored image data, by means of a trained neural network, other, or a combination thereof.

Subsequently, with the geometry of the coronary artery 281 for frames of the first set of image data known and location of the coronary artery 281 in the frames of the first set of image data known and frames of the first set of image data associated with frames of the second set of image data, geometry and location of the coronary artery 281 may be reconstructed in frames of the second set of image data, based on known data. The geometry and location of the coronary artery 182 may be reconstructed in the first subset and the second subset of the second set of image data or in only one of them.

To make efficient use of processing power, the geometry and location of the coronary artery 182 is reconstructed only in the first subset or second subset of the second set of image data. In step 224, step 226 and step 228, lengths of various images of the coronary artery 182 have been determined. In one implementation, the geometry and location of the coronary artery 182 is reconstructed only in the set that depicts the coronary artery 182 with a length closest to that of the lengths of the three-dimensional reconstruction of the coronary artery 182. In one example, this may be the subset that depicts the coronary artery having the longest length. The lengths used for this may be lengths of single—corresponding—frames from the first subset and the second subset. Alternatively, as the length of the coronary artery 182 may vary during a heartbeat, a mean or median value of the lengths may be used for this step.

As the coronary artery 281 is in the frames of the second set of image data not filled with contrast dye 150 or at least not fully filled, the coronary artery is not visible in the frames of the second set of image data and the reconstruction yields a ghost image of the coronary artery 281. It is noted that the location of the coronary artery 182 thus reconstructed in the frames of the second set of image data may not necessarily be the actual location of the coronary artery 182, but is rather an estimation of the location.

With the geometry and location of the coronary artery estimated in at least one of the first subset and second subset of the second set of image data available, the procedure proceeds to step 238, in which image data at and optionally near the estimated geometry and location of the coronary artery is monitored for change of intensity. For example, change of contrast may be evaluated at a pre-determined distance from a centreline of the reconstructed vessel. If the full vessel is reconstructed or a volumetric, three dimensional representation of the vessel is reconstructed or a two-dimensional reconstruction with a surface in a two dimensional space is provided, an area, volume, vessel width or other entity is monitored at a monitoring distance from the vessel, which monitoring distance is based on the volume or surface of the vessel at a particular location. The relation between the monitoring distance and the area, width or volume of the reconstructed vessel may for example be linear.

As contrast dye proceeds from a proximal point of the coronary artery 182—generally the aorta—to a distal point of the coronary artery 182—generally the endpoint —, the contrast of the image data changes along the estimated centreline of the coronary artery 182 in the frames of the second set of image data. In one example, only frames of the first subset are monitored, alternatively or additionally, frames of the second subset of the second set of image data are monitored. In one example, the subset is monitored in which frames depicted the coronary artery with the longest length and/or the length closest to the natural length of the coronary artery 182.

With the monitoring of change of intensity from frame to frame, over time, progress of the contrast dye in the coronary vessel 182 may be monitored. Subsequently, the velocity of fluid—contrast dye as well as blood—may be determined. This may, for example, be executed as discussed in patent application PCT/NL2021/050635.

The invention claimed is:

1. A method of monitoring a flow of a fluid in a vessel of a body of a living being, the method comprising:
   obtaining a first image data set representing the vessel filled with a first fluid, the first image data set comprising at least one first image frame and the first fluid contrasting with matter surrounding the vessel;
   obtaining a second image data set representing the vessel substantially void of the first fluid, the second image data set comprising at least one second image frame;
   based on the first image data set and the second image set, estimating an estimated location of the vessel in the second image set; and
   monitoring presence in the second image data set of contrasting image data at the estimated location of the vessel,
   wherein:
   the first image data set comprises a multitude of first image frames, the first image frames having been acquired consecutively in time; and
   the second image data set comprises a multitude of second image frames, the second image frames having been acquired consecutively in time;
   the method further comprising, over time;
   tracking, in the first image data set, the vessel;
   estimating, based on the tracking, a location of the vessel in the second frames of the second image data set, and
   reconstructing the vessel geometry.

2. The method according to claim 1, wherein:
   the first image data set is acquired over a first time interval relative to a heartbeat sequence;
   the second image data set is acquired over a second time interval relative to the heartbeat sequence; and
   the first time interval and the second time interval cover at least one equivalent part of the heartbeat sequence.

3. The method according to claim 1, wherein the first timer interval and the second timer interval cover at least one heartbeat sequence.

4. The method of claim 2, further comprising:
   aligning the first image data set and the second image data set based on heartbeat sequence data associated with the first image data set and the second image data set;

associating frames in the first image data set and the second image data set with a particular phase in the heartbeat sequence;

estimating, over time, estimated locations of the vessel in the second frames of the second image data set based on locations of the vessel in the first frames of the first image data set having substantially the same phase in the heartbeat sequence associated therewith as with the second frames.

5. The method of claim 4, wherein the first image data set and the second image data set have electrocardiogram data as heartbeat sequence data associated therewith.

6. The method of claim 4, wherein heartbeat sequence data is derived from image frame data in at least one of the first image data set and the second image data set.

7. The method according to claim 1, wherein the tracking of the vessel over time comprises:
identifying a multitude of points of interest distributed on a representation of the vessel in the first image frames; and
tracking locations of the points of interest in the applicable image over time.

8. The method according to claim 1, wherein the reconstructing comprises determining a centreline of the vessel in the image data.

9. The method according to claim 1, wherein the first image data set comprises:
a first image subset comprises at least a first image acquired under a first angle relative to the living being; and
a second image subset comprises at least a second image acquired under a second angle relative to the living being;
wherein the reconstructed vessel geometry is a three-dimensional geometry.

10. The method of claim 9, further wherein the second image data set comprises:
a first image subset comprises at least a first image acquired under the first angle relative to the living being; and
a second image subset comprises at least a second image acquired under the second angle relative to the living being;
wherein the estimated location of the vessel in the second image set is a three-dimensional location.

11. The method of claim 9, further comprising:
determining a first length of the vessel as depicted by the first image subset;
determining a second length of the vessel as depicted by the second image subset;
determining a natural length of the reconstructed vessel;
selecting the first image subset if the first length is closer to the natural length or selecting the second image subset if the second length is closer to the natural length;
estimating the location of the vessel in the second image data set based on the subset of the first dataset of which the length is closest to the natural length.

12. The method of claim 11, wherein the second image data set comprises:
a first image subset comprises at least a first image acquired under the first angle relative to the living being; and
a second image subset comprises at least a second image acquired under the second angle relative to the living being;
wherein the estimated location of the vessel in the second image set is a three-dimensional location, and
wherein the location in the second image data set is determined based on the image subset corresponding to the image subset of the first image data set depicting a length closest to the natural length.

13. The method according to claim 1, wherein the vessel is filling with the first fluid while the second dataset is acquired.

14. The method according to claim 1, further comprising estimating the location of the vessel in the second image data set by providing the first image data set to a trained neural network.

15. The method according to claim 1, wherein the second image data set is acquired prior in time relative to the acquiring the first image data set.

16. A computer programme product comprising computer executable code for causing a processor to execute the method according to claim 1.

17. A non-transitory computer readable medium having stored thereon the computer programme product according to claim 16.

18. A method of monitoring a flow of a fluid in a vessel of body of a living being, the method comprising:
obtaining a first image data set representing the vessel filled with a first fluid, the first image data set comprising at least one first image frame and the first fluid contrasting with matter surrounding the vessel;
obtaining a second image data set representing the vessel substantially void of the first fluid, the second image data set comprising at least one second image frame;
based on the first image data set and the second image set, estimating an estimated location of the vessel in the second image set,
monitoring presence in the second image data set of contrasting image data at the estimated location of the vessel;
reconstructing a vessel geometry based on the first image data set; and
estimating a location of the vessel in the second image set based on the first image data set and the reconstructed vessel geometry.

19. A method of determining vessel fluid flow velocity of a fluid in a vessel segment of a body of a human or another mammal, the method comprising:
obtaining a natural length model of the vessel representing a length of the vessel in accordance with the method according to claim 9;
obtaining a two-dimensional model of the vessel segment based on the first image dataset;
dividing the two-dimensional model in vessel sections;
receiving the second dataset comprising a multitude of second image frames, the second image frames having been acquired consecutively in time;
based on the images of the second dataset, assigning, for each image of the set, at least one intensity value to each vessel section;
identifying, in a first image related to a first moment in time, a first vessel section, based on an intensity criterion;
identifying, in a second image related to a second moment in time, a second vessel section, based on the intensity criterion, the second moment in time being later than the first moment in time and the second vessel section being distal to the first vessel section;

obtaining a propagation length by relating the first vessel section and the second vessel section to the natural length; and determining a vessel fluid flow velocity based on the propagation length, and a difference between the first moment in time and the second moment in time.

* * * * *